(12) United States Patent
Schultz et al.

(10) Patent No.: US 7,867,990 B2
(45) Date of Patent: Jan. 11, 2011

(54) STEROID HORMONE PRODUCTS AND METHODS FOR PREPARING THEM

(75) Inventors: Thomas Schultz, Richboro, PA (US); Bradley A. Clark, Gurnee, IL (US); Angela Falzone, Raritan, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 649 days.

(21) Appl. No.: 10/022,138

(22) Filed: Dec. 13, 2001

(65) Prior Publication Data

US 2002/0173669 A1 Nov. 21, 2002

(51) Int. Cl.
*A61K 31/56* (2006.01)
*C07J 41/00* (2006.01)
*A61K 9/14* (2006.01)
*A61K 9/16* (2006.01)

(52) U.S. Cl. ............... 514/182; 552/515; 552/516
(58) Field of Classification Search ......... 514/169, 514/177, 178, 182, 170, 179; 424/464; 552/648, 552/514, 610, 515, 516
See application file for complete search history.

(56) References Cited

U.S. PATENT DOCUMENTS

| | | | | |
|---|---|---|---|---|
| 2,636,042 A | * | 4/1953 | Salkin | 552/626 |
| 2,642,427 A | * | 6/1953 | Hasbrouck | 540/120 |
| 2,648,700 A | * | 8/1953 | Jacobsen et al. | 560/5 |
| 2,666,066 A | * | 1/1954 | Hasbrouck | 552/626 |
| 3,032,469 A | * | 5/1962 | Gleason | 514/182 |
| 3,691,212 A | * | 9/1972 | Feather et al. | 552/639 |
| 4,046,874 A | * | 9/1977 | Gabby et al. | 424/73 |
| 4,544,554 A | | 10/1985 | Pasquale | |
| 4,785,103 A | * | 11/1988 | Shibata et al. | 546/78 |
| 5,266,712 A | * | 11/1993 | Lanquetin | 552/574 |
| 5,342,627 A | * | 8/1994 | Chopra et al. | 424/473 |
| 5,382,434 A | | 1/1995 | de Haan et al. | |
| 5,407,928 A | * | 4/1995 | Kasch et al. | 514/179 |
| 5,527,543 A | * | 6/1996 | Dopper et al. | 424/489 |
| 5,633,242 A | * | 5/1997 | Oettel et al. | 514/170 |
| 5,720,977 A | * | 2/1998 | Deghenghi | 424/466 |
| 5,858,405 A | * | 1/1999 | Gast | 424/464 |
| 6,290,991 B1 | * | 9/2001 | Roser et al. | 424/502 |
| 6,495,532 B1 | * | 12/2002 | Bathurst et al. | 514/110 |
| 6,902,741 B1 | * | 6/2005 | Grawe et al. | 424/448 |

FOREIGN PATENT DOCUMENTS

| | | |
|---|---|---|
| EP | 0503521 A1 | 9/1992 |
| EP | 0587047 A | 3/1994 |
| EP | 0657161 A | 6/1995 |
| WO | WO 97/04750 A2 | 2/1997 |
| WO | 9804269 * | 2/1998 |

OTHER PUBLICATIONS

Nelson et al. (AN 74012246, Medline, J. of the National Cancer Institute, (1973), 51(4), 1303-11).*
Merck Index, 12th Edition, 1996, p. 632 (3751).*
Estrogens, Steroidal. Substance profiles: Report on Carcinogens, Eleventh Edition, 2002.*
Buckton et al.; "The influence of additives on the recrystallisation of amorphous spray dried lactose"; International Journal of Pharmaceutics, 121 (1995), pp. 81-87.
Huttenrauch et al.; "Mechanical Activation of Pharmaceutical Systems", Pharmaceutical Research 1985, pp. 302-306.
Lieberman et al.; "Pharmaceutical Dosage Forms", Marcel Dekker, Inc., vol. 2 (1990), pp. 213-217 and 327-329.
Morita et al.; "Physicochemical Properties of Crystalline Lactose. II$^1$. Effect of crystallinity on Mechanical and Structural Properties.", Chem. Pharm. Bull., 32(10) 1984, pp. 4076-4083.
Sebhatu et al.; "Assessment of the degree of disorder in crystaline solids by isothermal microcalorimetry", International Journal of Pharmaceutics 104 (1994), pp. 135-144.
Jain, et al.: "Stability of a hydrophobic drug in presence of hydrous and anhydrous lactose". European Journal of Pharmaceutics and Biopharmaceutics, Elsevier Science Publishers B.V., Amsterdam, NL., vol. 46, No. 2, Sep. 1998, pp. 177-182, XP004257039, ISSN: 0939-6411.

* cited by examiner

*Primary Examiner*—Sabiha Qazi
(74) *Attorney, Agent, or Firm*—Yuriy P. Stercho

(57) ABSTRACT

The present invention relates to steroid hormone products, such as oral contraceptive products, including at least one steroid active ingredient mixed with an excipient and having improved dissolution and release rate properties. The invention further relates to methods for making such steroid hormone products, wherein a mixture of the hormone and the excipient is subjected to sufficient mechanical energy to form a powder blend wherein the hormone is stabilized by the excipient in substantially non-crystalline form.

3 Claims, No Drawings

STEROID HORMONE PRODUCTS AND METHODS FOR PREPARING THEM

FIELD OF THE INVENTION

The present invention relates to steroid hormone products comprising at least one steroid active ingredient mixed with an excipient and having improved dissolution and release rate properties. More particularly, the invention provides an oral contraception product having an improved dissolution profile. The invention further relates to methods for making such steroid hormone products, either with or without the use of solvents.

As used herein, the term "steroid hormone product" is a physically discrete unit suitable as a unitary dosage for a human host. The product contains a predetermined quantity of at least one steroid active ingredient effective to produce a desired effect. Examples, of such products are tablets, capsules, caplets, pills or discrete quantities of powder.

BACKGROUND OF THE INVENTION

Oral contraceptives first became available in the early 1960's. Since then, a number of regimens for controlling ovulation and contraception by the administration of hormones have become known and are readily available. Oral contraceptive formulations typically contain an estrogen and a progestin. In addition to these steroid active ingredients, the formulation may contain an excipient including various grades of lactose, additives and fillers such as pregelatinized starch and magnesium stearate, and a colorant such as an aluminum oxide lake.

Solvent-based processes, referred to herein as "wet processing" have been commonly employed for many years to make commercial quantities of steroid hormone products, such as oral contraceptives containing steroid active ingredients, According to one well-known process, an active ingredient, such as a steroid hormone, is dissolved in an appropriate volatile solvent and sprayed onto a bed of a pharmaceutically acceptable excipient powder until a desired concentration of the active ingredient per unit weight of powder is achieved. In general, the solvent employed is compatible with the active ingredient and the chosen excipient and can be removed under conditions that will not result in the degradation of the active ingredient. Particularly suitable solvents for use with steroid hormone active ingredients include alcohols such as methanol, ethanol and propanol, ketones such as acetone, hydrocarbons such as ethylene chloride and chloroform, and mixtures of one or more of these solvents with water. The solution is typically sprayed onto the bed of excipient powder in a suitable processor, such as a V-blender with an intensifier bar or a fluid bed processor. The solution and powder are then thoroughly mixed in the processor to ensure uniform dispersion of the active ingredient in the excipient. After mixing, the solvent is removed by the application of heat and/or vacuum to provide a dry mixture.

In an alternative wet processing technique, referred to by those skilled in the art as high sheer wet granulation, the solvent is not sprayed onto the excipient but is, instead, mixed directly with the excipient powder in a high shear blender. Subsequent to mixing, the solvent is removed as described above to provide a dry mixture.

Wet processing provides a number of advantages, including powder blends that have a uniform distribution of active ingredient and that suffer only minimal segregation under usual conditions of storage and handling. Steroid hormone products prepared from these blends typically exhibit excellent content uniformity.

A major disadvantage of these solvent-based processes is that environmentally objectionable organic solvents are generally required in those cases where the steroid active ingredient has poor water solubility. Such solvents often pose safety hazards during handling, in addition to the hazards they present when they are released into the environment. Increasingly, health regulatory authorities are objecting to the use of such solvents due to their toxicity and mutagenicity.

Accordingly, a dry granulation or direct compression process would be preferable for active ingredients that would generally otherwise require the use of an organic solvent. Such dry granulation or direct compression processes will be referred to herein as "dry processing". Dry processing generally involves fewer steps than solvent-based wet processing and does not require elevated temperatures that can reduce the potency of temperature-sensitive active ingredients. Dry processing is also especially suitable for products that include steroid hormones sensitive to the moisture associated with wet processing via aqueous granulation. The absence of expensive organic solvents and the required evaporation steps also makes dry processing economically more attractive.

U.S. Pat. No. 5,382,434 has proposed pharmaceutical preparations containing steroids (e.g., progestin and/or estrogen) and an excipient (e.g., lactose) made without the use of solvents. According to the '434 patent, at least 80% of the steroid must be bound to the excipient and the excipient must have a low "demixing potential," which is a measure of content uniformity. The excipient is mixed with the steroid until a uniform mixture is obtained. However, the '434 patent is silent as to release characteristics of these compositions and teaches only a mechanical interaction during the mixing operation.

As those skilled in the art recognize, known steroid hormone products present a number of disadvantages that are not addressed by either wet or dry processing techniques. Steroids exist in various polymorphic forms, defined here to include crystalline, amorphous and solvate forms. In the case of wet processing, the inability to identify the polymorphic form(s) of the potent steroid(s) that exists in a steroid hormone product following removal of the deposited organic solvent is a potential concern both from a physical/chemical stability prospective and from a biopharmaceutical prospective. Unfortunately, known methods of dry processing do not completely eliminate the potential existence of polymorphic forms.

In addition, steroid hormone products prepared by either wet or dry processing methods may present bioavailability problems. Before a drug that is orally administered as a solid can be absorbed, it must first dissolve in the gastrointestinal medium, and then it must be transported in the dissolved state across the gastrointestinal mucosa into the blood stream. As a surrogate test to predict bioavailability prior to commercial release of a drug product, regulatory authorities routinely require that at least 80% of the active ingredient in the product dissolve within 60 minutes in a "physiologically relevant" medium, i.e., a dissolution medium for in-vitro testing. Low dose steroid formulations prepared by known methods of either wet or dry processing have exhibited an undesirable variability in release rate, as measured by dissolution rate techniques in an aqueous medium containing a surfactant. Notably, upon scale up, formulations containing low dose steroids manufactured by dry processing and intended for use as oral contraceptives routinely had slower dissolution rates or at least suffered from a poorly reproducible dissolution profile.

Steroid hormones such as estrogen and progestin are also employed for hormone replacement therapy (HRT). Steroid hormone products used for HRT may contain up to a ten fold higher amount of estrogen and, typically, a lesser amount of progestin than oral contraceptives. Consequently, it is anticipated that such products may experience similar problems related to dissolution. Accordingly, it would also be desirable to reduce or eliminate such problems in the case of HRT steroid hormone products.

SUMMARY OF THE INVENTION

In accordance with the invention, a steroid hormone product having an improved dissolution profile and release rate profile is provided. The product comprises at least one steroid hormone in substantially non-crystalline form in admixture with primary excipient, wherein the excipient stabilizes the steroid in its substantially non-crystalline form. The hormone products taught by the invention are characterized by highly favorable dissolution properties. The preferred excipient is lactose, although it should be understood that the invention is in no way limited in this regard and other excipients well-know in the art may be utilized, including dextrose, fructose, sorbitol, xylitol, sucrose, mannitol, dextrate, cellulose, starch and combinations of two or more of the foregoing.

The steroid hormone products of the invention are particularly useful as either oral contraceptives or HRT products. In a preferred embodiment of this aspect of the invention, the steroid hormone product is an oral contraceptive comprising from about 10 µg to about 50 µg of an estrogen and/or from about 50 µg to about 300 µg of a progestin. The progestin is preferably either norgestimate, norgestrel, levonorgestrel, norethindrone or desogestrel, and the estrogen is preferably either ethinyl estradiol, estradiol, estopipate or mestranol.

In a second aspect, the invention provides a method of preparing such a steroid hormone product, which method comprises preparing a mixture of at least one steroid hormone and an excipient, preferably lactose, and imparting to said mixture mechanical energy sufficient to yield an excipient/steroid powder blend in which the steroid is stabilized by the excipient in a substantially non-crystalline form. Preferably, at least about 0.1 hp-min/kg of mechanical energy is imparted to the mixture. Any method of high energy processing may be employed to impart sufficient mechanical energy to carry out the process of the invention. One preferred method of imparting sufficient mechanical energy involves high energy blending of the lactose and steroid, but other high energy mixing processes known in the art may be employed such as co-grinding or milling the mixture.

Preferably, the mixture is prepared with a steroid hormone to excipient ratio in the range of from about 1/1 to about 1/10. However, it should be understood that the invention is in no way limited in this regard and other hormone/excipient ratios may be employed depending on the desired concentration of hormone in the final product. Typically, the ratio of steroid to excipient in the mixture is the same as that required for the final product. However, it should be understood that an initial mixture of steroid hormone and excipient may be prepared, with additional excipient added subsequently to produce a final mixture. The final mixture is then subjected to high energy processing to impart sufficient mechanical energy to carry out the invention.

In one preferred embodiment of the invention, the steroid/excipient mixture is formed by standard wet processing. For example, a solution of at least one steroid hormone dissolved in an appropriate solvent is prepared and then sprayed onto the excipient powder. The solution and excipient are mixed in a suitable processor to ensure uniform distribution of the solvent in the excipient. The resulting mixture is then dried by removing the solvent via the application of heat and/or vacuum. Mechanical energy is then imparted to the mixture as described above to provide the steroid/excipient powder blend. In another preferred embodiment of the invention, the steroid and excipient are mixed by standard dry processing and mechanical energy is then imparted to the mixture as described above to provide the steroid/excipient powder blend.

DETAILED DESCRIPTION

As used herein, the following terms shall have the meaning ascribed to them below, except when the context clearly indicates differently:

"Poor" or "low" solubility refers to substances that are very slightly soluble to insoluble according to the following USP definitions.

| USP Descriptive Term | Part of Solvent Required for 1 Part of Solute | Equivalent mg/mL |
|---|---|---|
| Sparingly Soluble | From 30 to 100 | 33.3 mg/mL-10 mg/mL |
| Slightly Soluble | From 100 to 1000 | 10 mg/mL-1 mg/mL |
| Very Slightly Soluble | From 1000 to 10000 | 1 mg/mL-0.1 mg/mL |
| Practically Insoluble, or Insoluble | 10000 and over | $\leq$0.1 mg/mL |

"Content uniformity" means a relative standard deviation in active ingredient content of ±1.5%, preferably ±1.0% and most preferably ±0.5%.

As stated above, it is known that steroid hormones such as estrogens and progestins can exist in various solid state forms and that the particular form of the steroid may significantly effect properties such as dissolution rate and physical/chemical stability. An increase in dissolution rate and the extent of dissolution, as well as a decrease in physical/chemical stability are two potential consequences of modifying the stable crystalline form of these steroid hormones. In general, the higher energy, non-crystalline solid state form will exhibit an increase in dissolution rate over the more stable, lower energy crystalline form.

This is also the case with certain excipients such as lactose. Lactose is commonly selected as an excipient in tablets and capsules. It is commercially available in an assortment of grades including anhydrous α lactose, α lactose monohydrate, anhydrous β lactose and spray-dried lactose. Spray-dried lactose (e.g., FAST-FLO lactose available from Foremost Farms, Baraboo, Wis.) is commonly selected as an excipient in direct compression formulations due to its superior flow and compression characteristics. This grade of lactose predominately contains pure α lactose monohydrate in combination with non-crystalline lactose. The non-crystalline component enhances the compressibility of lactose. Morita et al., "Physiochemical Properties of Crystalline Lactose, II. Effect of Crystallinity on Mechanical and Structural Properties", *Chem. Pharm. Bull.*, Vol. 32, p. 4076 (1984). The non-crystalline state is metastable in nature and recrystallization to a more thermodynamically stable form is inevitable. The tendency for non-crystalline lactose to rapidly recrystallize upon exposure to relative humidity greater than approximately 60% is well documented. Sebhatu et al., "Assessment of the Degree of Disorder in Crystaline Solids by Isothermal Microcalorimetry", *International Journal of Pharmaceuticals*, Vol. 104, p. 135 (1994). However for many drug substances, this process can be delayed by the addition of such materials as microcrystalline cellulose, polyvinylpyrrolidone or citric acid. Buckton et al., "The Influence of Additives on the Recrystallization of Amorphous Spray-Dried Lactose", *International Journal of Pharmaceuticals*, Vol. 121, p. 81 (1995).

Various unit operations are routinely employed during the manufacture of conventional steroid hormone products, including milling, blending, wet granulation, drying and compression. Each process is associated with the incorporation of mechanical and/or thermal energy into the system. Consequently, the potential for modification of various solid state properties of steroid active ingredients and excipients exists. Hüttenraunch, et al., "Mechanical Activation of Pharmaceutical Systems", *Pharmaceutical Research*, Vol. 2, p. 302 (1985). As noted above, such changes may significantly alter properties such as dissolution rate and dissolution extent, as well as physical/chemical stability (e.g., conversion to a different solid state form, hydrolysis, etc). Increases in dissolution rate and extent and a decrease in physical/chemical stability are two potential consequences of modifying the stable crystalline form of a material. However it would be highly desirable to increase the dissolution rate while either improving or at least not reducing the physical/chemical stability. The probability of encountering such crystalline form modifications during dosage form processing is directly related to the propensity of each ingredient to exist in a variety of polymorphic forms.

Norgestimate is a potent progestational agent. A thorough investigation of the polymorphic potential of this substance demonstrated the existence of at least two solid state forms, a stable crystalline form and a relatively higher energy non-crystalline form. It is also known that a relatively higher energy non-crystalline form of lactose exists in addition to the stable crystalline form routinely employed in tablet manufacture. Similar to lactose, the higher energy non-crystalline form of norgestimate can be generated via physical or mechanical processes. The present inventors have found that non-crystalline norgestimate can be physically generated from solution subsequent to the rapid evaporation of various organic solvents. Laboratory experiments clearly demonstrate that non-crystalline norgestimate can also be generated by ball milling. An obvious reduction in norgestimate crystallinity can be observed within 5 minutes of milling. Considering the relative ease of crystalline structure modification via mechanical energy, as well as the inherent non-crystalline lactose content in conventional lactose preparations, it was hypothesized that co-processing of lactose and norgestimate could result in the generation of a solid solution. In theory this solid solution would consist of non-crystalline norgestimate solubilized within the non-crystalline domains of lactose resulting in a composition exhibiting a more rapid dissolution rate and possibly enhanced physical/chemical stability.

Research efforts were thus made to generate the non-crystalline form of norgestimate in the presence and absence of lactose via physical and mechanical processes. Various mixtures of norgestimate and lactose were prepared. To permit qualitative or semi-quantitative analysis, the ingredients were thoroughly mixed in ratios of 1:1 and 1:9 by either dissolving them in a co-solvent mixture or by co-grinding. Qualitative assessment of the degree of crystallinity was performed employing Powder X-Ray Diffractometry (PXRD). The minimum detectable level of crystalline norgestimate in this solid mixture was demonstrated to be approximately 3%.

The physical stability of non-crystalline norgestimate and non-crystalline lactose were assessed prior to investigation of the drug/excipient interaction. Room temperature storage conditions employed at various relative humidities (% RH) of 0%, 31% and 76% RH were employed. Complete recrystallization of amorphous norgestimate was observed within 3 days at all conditions tested. Based on these data, the ability of lactose to inhibit recrystallization and enhance the physical stability of non-crystalline norgestimate was investigated.

Co-precipitation of norgestimate and FAST-FLO lactose from a solvent mixture of ethanol and water was achieved by solvent evaporation under reduced pressure. In the presence of lactose, norgestimate remained totally amorphous for at least 32 days at room temperature in a 0% RH chamber. Norgestimate recrystallized within 3 days in the absence of lactose under the same conditions. As anticipated, PXRD analysis of both the 1:1 and 1:9 norgestimate: FAST-FLO lactose mixtures made in this manner demonstrated recrystallization of lactose within 1 hour at 75% RH. This was anticipated since non-crystalline lactose undergoes rapid recrystallization at approximately 60% RH. Sebhatu et al., supra. However, the norgestimate remained partially non-crystalline for at least 6 days at this high relative humidity. The fact that norgestimate remains in a non-crystalline form subsequent to the recrystallization of lactose implies that the two compounds are miscible in the solid state. These findings further support the hypothesis that a metastable solid solution is formed between lactose and norgestimate when dissolved in a hydro-alcoholic system and co-precipitated.

In an attempt to more closely mimic the process employed in the manufacture of steroid hormone tablets by dry processing, 1:9 crystalline norgestimate/FAST-FLO lactose mixtures were ball milled together for 20 minutes. PXRD analysis indicated an absence of crystalline norgestimate. However no visually obvious reduction in the crystallinity of lactose was observed. The milled mixture was stored at room temperature at 0% RH and at 31% and 40° C. at 75% RH. Based on visual observation, norgestimate remained in a non-crystalline form at room temperature for at least 103 days in this mixture. Recrystallization of norgestimate at the accelerated temperature/humidity condition was initiated between 54 and 82 days. These data further support the hypothesis that a non-crystalline form of norgestimate is physically stabilized by lactose even in the absence of detectable modification in the crystallinity of lactose. One would also anticipate a more rapid dissolution of norgestimate from a solid solution than from the crystalline form.

Employing the current dissolution standard (USP Apparatus 2, 75 rpm, 600 ml of 0.05% Tween 20), the dissolution rates and extent of dissolution for individual samples of both crystalline and non-crystalline norgestimate were compared. Not surprisingly, this preliminary investigation demonstrated a difference in dissolution behavior of the two solid state forms of norgestimate. The results of the study are set forth below in Table 1.

TABLE 1

| Dissolution Time (min.) | Amorphous Norgestimate | Crystalline Norgestimate |
|---|---|---|
| 5 | 0.44 ug/mL | 0.43 ug/mL |
| 60 | 1.38 ug/mL | 0.81 ug/mL |
| 120 | 1.88 ug/mL | Not Determined |
| 140 | Not Determined | 1.36 ug/mL |

The dissolution rate and extent of norgestimate dissolution subsequent to co-milling with lactose at a ratio of 1:9 was also evaluated. PXRD indicated that norgestimate was rendered non-crystalline while lactose was rendered partially crystalline following milling. Employing a 100 ml volume of 0.05% Tween 20 as a medium, dissolution characteristics of norgestimate were determined as a function of storage time at approximately 40° C. at 75% RH. PXRD was employed to follow the recrystallization kinetics of the solid solution formed. As anticipated, lactose recrystallized between 0 and 2 days. Initiation of norgestimate recrystallization was noted between 17 and 22 days. Norgestimate remained partially crystalline for at least 44 days under the accelerated storage conditions. The results of the evaluation are set forth in Table 2.

TABLE 2

| Dissolution Time (min.) | Norgestimate Concentration Time = 0 Days | Norgestimate Concentration Time = 44 Days |
|---|---|---|
| 10 | 5.3 ug/mL | 2.4 ug/mL |
| 20 | 5.1 ug/mL | 5.2 ug/mL |
| 30 | 6.2 ug/mL | 6.5 ug/mL |
| 60 | 8.7 ug/mL | 5.9 ug/mL |
| 240 | 10 ug/mL | 6.7 ug/mL |
| 720 | 10.3 ug/Ml | 7.3 ug/mL |

These data demonstrate that the dissolution properties of norgestimate in combination with lactose (1:9 ratio) change as norgestimate begins to recrystallize from the metastable solid solution. These data further demonstrate the potential influence of mechanical energy on the solid state form of norgestimate and lactose in norgestimate tablets.

Differences in the dissolution behavior of norgestimate from tablets manufactured by dry processing on both a pilot scale and a production scale were also evaluated. The minimum mechanical energy of 0.1 hp-min/kg can be imparted in a dry process using a geometric tumbler blender equipped for additional mixing energy with blades or choppers. A progestin such as norgestimate can be combined with lactose and additives. Increasing the length of processing time with the blades or choppers in use would impart sufficient energy to produce the forms identified in this invention. The results of a dissolution rate study at two different equipment scales is presented in Tables 3a and 3b. With an increase in dissolution rate being an indirect measure of the presence of the invention, the data indicate higher levels of the less crystalline progestin as greater energy is imparted over time. The important of dissolution rate as a function of mixing time is also noted. The results of the evaluation are reported in Tables 3a and 3b, respectively.

TABLE 3a

| Pilot Scale Mixing Time (Minutes) | Percent Norgestimate Dissolved in 20 Minutes |
|---|---|
| 2.5 | 74.9 |
| 5 | 78.4 |
| 10 | 85 |
| 20 | 88.5 |
| 30 | 97.4 |
| 33 | 93.6 |

TABLE 3b

| Production Scale Mixing Time (Minutes) | Percent Norgestimate Dissolved in 20 Minutes |
|---|---|
| 4.8 | 64.7 |
| 12 | 81.2 |
| 15 | 90.3 |

TABLE 3b-continued

| Production Scale Mixing Time (Minutes) | Percent Norgestimate Dissolved in 20 Minutes |
|---|---|
| 30 | 92.8 |
| 45 | 96.2 |
| 60 | 97.4 |
| 75 | 97.2 |

As the data set forth below in Table 4 demonstrate, the relative stability of dissolution properties of tablets manufactured by wet processing and stored unprotected under accelerated conditions are also sensitive to changes in mixing energetics. The data in Table 4 further support the existence of a high energy form of norgestimate in the presence of lactose. In addition, changes in dissolution behavior when stored at 40° C. at 75% RH is demonstrated in Table 4. Like the data reported in Table 2, dissolution properties are dependent on storage conditions. However it is apparent that the extent of such changes is further dependent on the mixing energetics imparted during the process.

TABLE 4

| Blend Time | Percent Norgestimate Dissolved in 30 Minutes | |
|---|---|---|
| (minutes) | Initial | 1 month 40° C./75% RH |
| 0 | 75.4 | 36 |
| 2* | 91 | 45 |
| 20 | 90.1 | 45 |
| 40 | 92.6 | 46 |
| 60 | 94.5 | 85 |

Based on the studies reported above, it has been determined that when a mixture of an excipient and a steroid active ingredient form a less crystalline, more highly energetic composition. Furthermore, under appropriate mixing conditions, the lactose component stabilizes the steroid in a highly energetic, substantially non-crystalline state, thus preventing recrystallization of the steroid. This is particularly important in the case of a progestin such as norgestimate that is quite unstable in the non-crystalline form and prone to rapid recrystallization. The highly energetic, non-crystalline steroid active ingredient dissolves more readily and is better to maintain desirable dissolution characteristics under a variety of conditions of ambient humidity and ambient temperature. In addition it has been demonstrated that the high-energy steroid: lactose mixture has a higher recrystallization temperature than the same steroid lactose mixture has under conditions where it has not been subjected to high energy mixing and where the mixture components remain in the amorphous state. (Table 7, Example 3)

As noted previously, preferably at least about 0.1 (hp-min)/kg of mechanical energy is imparted to the mixture, most preferably at least about 0.12 (hp-min)/kg of mechanical energy. Any method of high energy processing may be employed to impart sufficient mechanical energy to carry out the process of the invention. One preferred method involves high energy blending carried out in equipment which is able to impart the energy level needed to achieve the invention. Examples of such equipment include a geometric tumble blender with an intensification system, a bowl type blender with high shear blade or impeller or a ribbon blender with appropriate energy capacity. The blending system would be operated with parameters appropriate to deliver the energy necessary to achieve the invention. Alternatively, grinding or milling, may be employed. This is accomplished in a commonly available mill grinder. Milling conditions can vary within a substantial range, typically the mixture is milled for a period of 10-30 minutes, preferably about 20 minutes when a small mill with a ball is employed.

Although not critical, it is preferable to control humidity before and during the mixing operation to 55% relative humidity or lower to further inhibit crystallization of the components, and mixing is also preferably conducted at an ambient temperature.

As also noted previously, additional ingredients may be added to the mixture, preferably such ingredients are added to the excipient powder prior to the high energy mixing operation. Typically employed ingredients include: (i) disintegrants such as clays, alginic acid and alginates, celluloses such as microcrystalline cellulose, croscarmellose sodium, cross-linked polymers such as cross-linked polyvinylpyrrolidone (crospovidone) or cross-linked sodium carboxymethylcellulose, and polacrilin potassium, starches such as sodium starch glycolate, starch and pregelatinized starch; (ii) lubricants such as talc, magnesium stearate, calcium stearate, stearic acid, colloidal silicon dioxide, magnesium carbonate, magnesium oxide, calcium silicate; and (iii) colorants such as caramel, D&C and FD&C dyes, for example. Other additional ingredients include glidants, fillers, binders and the like. The foregoing additional ingredients, as well as any other excipients or processing aids, can be added as required to yield a material suitable to be processed into a steroid hormone product.

The process of this invention is most suitable for the preparation of oral contraceptives containing one or more steroids, preferably a progestin, most preferably norgestimate, and/or an estrogen preferably ethinyl estradiol as the active ingredient(s). Instead of norgestimate, oral contraceptives containing norgestrel, levonorgestrel, desogestrel, 3-ketodesorgestrel, or norethindrone as the progestin can be prepared by the present invention. The oral contraceptives may also contain an estrogen compound such as β-estradiol, ethinyl estradiol, 17-αethinyl estradiol, 3-methyl ether estropipate and mestranol. However, the process has applicability to the preparation of any pharmaceutical preparation which contains as the active ingredient, a material having low to moderate solubility in water and which exists in a variety of polymorphs some of which may be stabilized via a physical interaction with an excipient such as lactose to yield a more rapidly soluble material. Furthermore, the process is particularly applicable to the preparation of oral contraceptives containing within a kit solid oral dosage forms of varying potency as to a particular active ingredient, as described above. Alternatively, the process of the invention can be used to prepare HRT products which also contain an estrogen and/or a progestin generally in different active ingredient amount combinations than the oral contraceptives.

The following examples describe the invention in greater detail and are intended to illustrate it without limiting its scope.

EXAMPLE 1

Amorphous Lactose/Norgestimate Dry Ground Mixture

Amorphous norgestimate was prepared by dissolving norgestimate (200 mg) in 5 ml of (DCM) dichloromethane and 0.26 ml ethanol (EtOH). The solution was filtered through a 0.2 μm filter, and solvent was evaporated under reduced pressure to afford amorphous solid.

Mixtures of norgestimate and lactose, in amorphous and crystalline forms, were milled for 20 minutes. The amorphous state of each ingredient and of the mixture was confirmed by powder x-ray pattern diffraction (PXRD). The results are described below and summarized in Table 5.

A mixture of crystalline norgestimate:crystalline lactose (1:9) was milled in a Wig-l-Bug mill. A small mill containing a ball afforded amorphous norgestimate with mostly crystalline lactose, whereas a larger mill containing a bar yielded both as crystalline materials. Milling a 1:1 mixture of crystalline norgestimate:crystalline lactose afforded partially crystalline norgestimate with mostly crystalline lactose.

A mixture of amorphous norgestimate and amorphous lactose (1:9) was milled also. The resulting solid mixture showed an amorphous PXRD pattern for both components. Milling 1:1 mixtures of amorphous norgestimate and amorphous lactose also afforded non-crystalline mixtures.

TABLE 5

Preparation of Amorphous Norgestimate: Lactose by Milling

| Method[a] | Norgestimate: Lactose | Sample No. | PXRD Pattern[b] Norgestimate | PXRD Pattern[b] Lactose |
|---|---|---|---|---|
| WLB (30 m) | 1:9[c] | 161-55-01[d] | C | C |
| WLB (20 m) | 1:1[c] | 256-33-1[e] | PC | C |
| WLB (20 m) | 1:9[c] | 256-33-03[e] | A | C |
| WLB (20 m) | 1:1[f] | 268-25-01[d] | A | A |
| WLB (20 m) | 1:1[f] | 314-10-01[d] | A | A |
| WLB (20 m) | 1:9[f] | 268-24-01[d] | A | A |

[a]Solid was milled using a Wig-L-Bug ® (WLB) mill for the specified time in minutes.
[b]C = crystalline; A = amorphous; PC = partially crystalline.
[c]Both crystalline samples were used.
[d]Small Wig-L-Bug ® mill containing a ball was used.
[e]Large Wig-L-Bug ® mill containing a bar was used.
[f]Both amorphous samples were used.

EXAMPLE 2

Stability Studies of Amorphous Materials

This study shows that amorphous norgestimate is stabilized by lactose in a number of norgestimate:lactose preparations. Stress studies as well as thermal analyses (Example 3) showed the stabilization of norgestimate in norgestimate:latose mixtures.

Amorphous norgestimate was prepared from DCM:EtOH solution, and its stability was studied under various humidity conditions to establish a baseline of norgestimate stability. In order to simulate drug products, non-crystalline norgestimate:lactose mixtures were obtained from one of the following four methods: co-precipitation from EtOH:H₂O, or 2-BuOH:H₂O, spray drying onto amorphous lactose, milling of crystalline mixtures, or milling of amorphous mixtures. The physical stability of non-crystalline norgestimate to resist recrystallization was also studied in the absence of and with an equal amount of lactose.

The materials for each sample were prepared as follows:

Amorphous Norgestimate

Norgestimate (200 mg) was dissolved in 5 mL of DCM and 0.26 mL of ethanol. The solution was filtered through a 0.2 μm filter and solvent was evaporated under reduced pressure to afford the amorphous solid.

Amorphous Lactose

FAST-FLO lactose (516 mg) was dissolved in 17 mL of $H_2O$ and filtered through a 0.2 µm filter, then lyophilized to afford dry material. However, the solid was partially crystalline.

Co-precipitation of Norgestimate/Lactose

Norgestimate (10 mg) and FAST-FLO lactose (91 mg) were dissolved in 143 mL of $EtOH:H_2O$ (3.56:1) and filtered through a 0.45 µm filter. The solvent was evaporated under reduced pressure to afford amorphous solid.

Norgestimate (20 mg) and FAST-FLO lactose (180 mg) were dissolved in 65 mL of 2-Butanol:Water (68:32) and filtered through a 0.2 µm filter. The solvent was evaporated under reduced pressure at 30° C. to afford a non-crystalline solid.

Norgestimate (10 mg) and FAST-FLO lactose (90 mg) were dissolved in 29 mL of $ACN:H_2O$ (2.6:1) at 60° C. and filtered through a 0.2 µm filter. The solvent was evaporated under reduced pressure at 35° C. to afford a non-crystalline solid.

Spray Drying of Norgestimate/Lactose

Amorphous lactose was placed in a round bottom flask and attached to a vacuum pump. A solution of norgestimate in 95:5 $EtOH:H_2O$ (0.5 mg/mL) was filtered through a 0.2 µm filter and sprayed into the round-bottom flask containing lactose while the vacuum was applied. The solution of norgestimate dried on the surface of the lactose solid to afford non-crystalline norgestimate.

A solution of amorphous lactose in methanol was applied on silica gel TLC and observed under a short-wave UV lamp. An UV active spot was observed. Lactose alone showed no UV active spots.

Milling of Norgestimate/Lactose

Norgestimate (50 mg) and FAST-FLO lactose (450 mg) were placed in a Wig-L-Bug mill, and milled with a bar for 20 minutes to afford non-crystalline norgestimate.

Physical Mixing of Norgestimate/Lactose

Norgestimate (2.2 mg) and lactose (2.6 mg) were mixed with a spatula in a vial for 1 minute. Additional amounts of lactose (4.6 mg) were added and then mixed with a spatula for another minute. This was repeated until all of the lactose was added (9.0 mg, 2.6 mg, total of 18.8 mg).

Stability Studies of Amorphous Material

A vial containing a small amount of amorphous material was placed in a humidity chamber containing an aqueous salt solution and the chamber was sealed. The sample was analyzed at specified time points by PXRD.

PXRD

PXRD analyses were carried out on a Shimadzu XRD-6000 X-ray powder diffractormeter using Cu Kα radiation (1.5406.A). The instrument is equipped with a fine-focus X-ray tube. The tube voltage and amperage was set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3/min (0.4 sec/0.02 step) from 2.5 to 40° 2Ø was used. A silicon standard was analyzed each day to check the instrument alignment. Each sample was analyzed on a quartz sample holder.

Table 6 summarizes the results of the stability studies. The data demonstrate that the simulated drug products of this invention show superior physical stability compared to amorphous norgestimate alone. In the absence of lactose, amorphous norgestimate recrystallizes in less 3 days at 0% relative humidity and less than 1 day at 31% and 76% relative humidities. Co-precipitates from $EtOH:H_2O$ or $2-BuOH:H_2O$ show stability (ie. onset of norgestimate recrystallization) to 90 days or 25 days, respectively, at 0% RH. In spray-dried or milled mixtures, norgestimate remained essentially non-crystalline during the entire study period (97 days) at 0% or 31% RH. A milled mixture showed the best stability at 76% RH, stabilizing non-crystalline norgestimate up to about 82 days. A 1:1 milled amorphous mixture showed partially crystalline norgestimate and after 93 days it remained partially crystalline. From these studies, it can be concluded that lactose stabilized norgestimate in an essentially non-crystalline form.

TABLE 6

Stability of Amorphous Norgestimate

| Amorphous Sample | Method | Stability of Amorphous Norgestimate | | |
|---|---|---|---|---|
| | | 0% RH | 31% RH | 76% RH |
| Norgestimate | Evaporated | <3 days | <1 day | <1 day |
| 1:9 Norgestimate:Lactose | Co-precipitated from $EtOH:H_2O$ | <90 days | — | <1 day |
| 1:1 Norgestimate:Lactose | Co-precipitated from $EtOH:H_2O$ | — | — | <7 days |
| 1:9 Norgestimate:Lactose | Co-precipitated from $2-BuOH:H_2O$ | <25 days | <6 days | <1 day |
| 1:9 Norgestimate:Lactose | Spray-dried from $EtOH:H_2O$ | >97 days | >97 days | — |
| 1:9 Norgestimate:Lactose | Milled crystalline mixture | >103 days | >103 days | <82 days |
| 1:9 Norgestimate:Lactose | Milled amorphous mixture | >93 days | >93 days | <1 day |
| 1:1 Norgestimate:Lactose | Milled amorphous mixture[h] | <1 day[i] | <1 day[i] | <1 day |

EXAMPLE 3

The lactose/norgestimate mixtures made as in Example 2 were subjected to thermal analysis, according to conventional Differential Scanning Calorimetry (DSC).

Glass-Transition Temperature and Crystallization Exotherm Measurements

Amorphous materials exhibit glass-transition temperatures ($T_g$) that reflect the physical stability of the amorphous form. The stabilized mixtures, norgestimate:lactose (1:9) mixtures, were examined along with individual amorphous materials to obtain $T_g$ values that might give insight to the stability of each mixture compared to a single-component system. Glass-transition temperature measurements generally entail trial runs on a DSC to obtain an optimal method for observing glass-transition events. Amorphous lactose exhibits a very strong $T_g$ event at 114-115° C. However, amorphous norgestimate does not produce consistent $T_g$ events. Some amorphous norgestimate samples produce a weak $T_g$ event at 122-123° C., while other samples shown an exothermic event, probably because of norgestimate crystallization. All of the norgestimate samples show a similar endothermic event at 226-228° C. The thermal gravimetric analysis (TGA) of samples show rapid weight loss at that temperature, therefore, the endotherm over 220° C. primarily corresponds to decomposition. The Merck Index lists the melting temperature of the crystalline norgestimate at 214-218° C.

Another DSC method used revealed a consistent thermal event corresponding to the crystallization of norgestimate (Tc). This thermal event (Tc) was used to measure the stability of different simulated drug products. The temperature of Tc- should be higher if norgestimate is stabilized by lactose.

The simulated drug products show the absence or a higher crystallization event ($T_c$) compared to pure amorphous norgestimate (Table 7). The $T_c$ data are consistent with the physical stability data, proving that amorphous norgestimate stabilization is achieved by lactose.

TABLE 7

$T_c$ Measurements of Amorphous Mixtures

| Sample | $T_c$ |
|---|---|
| Amorphous norgestimate | 105° C. |
| 1:9 Norgestimate:lactose co-precipitate from 2-BuOH:$H_2O$ | 164° C. |
| 1:1 Norgestimate:lactose co-precipitate from 2-BuOH:$H_2O$ | |
| 1:9 Norgestimate:lactose spray-dried | |
| 1:9 Crystalline norgestimate:lactose milled | 132° C. |
| 1:9 Amorphous norgestimate:lactose milled | |
| 1:1 Amorphous norgestimate:lactose milled | 126° C. |

EXAMPLE 4

Wet/Dry Processing

A progestin such as norgestimate is dissolved in an appropriate solvent such as methanol or ethanol. The solution is then deposited onto a powder bed containing lactose and several other additives. The deposition involves creating droplets of the solution which are sprayed onto the powder bed with mixing to prevent lumps. After sufficient time for all the solution to be deposited the solvent is removed using vacuum and heat. When a predetermined minimum quantity of solvent has been removed, the mixture is then subjected to further blending. The blending is performed, for example, in a geometric tumble blender equipped with an impeller or chopper blades for a length of time sufficient to impart mechanical energy as described above to produce a lactose/progestin powder blend with the progestin stabilized in substantially non-crystalline form.

What is claimed is:

1. An oral steroid hormone product having improved dissolution and release rate properties, said product comprising norgestimate in admixture with lactose, wherein substantially all of said norgestimate is in non-crystalline form and wherein said lactose stabilizes said norgestimate in its non-crystalline form.

2. The steroid hormone product of claim 1, wherein the product is one of an oral contraceptive product and a hormone replacement therapy product.

3. The steroid hormone product of claim 2, wherein the product is an oral contraceptive product comprising from about 10 µg to about 50 ug of an estrogen and/or from about 50 µg to about 300 µg of norgestimate.

* * * * *